United States Patent [19]

McMichael

[11] Patent Number: 4,966,753

[45] Date of Patent: Oct. 30, 1990

[54] IMMUNOTHERAPEUTIC METHODS AND COMPOSITIONS EMPLOYING ANTIGENS CHARACTERISTIC OF MALIGNANT NEOPLASMS

[75] Inventor: John McMichael, Cambridge Springs, Pa.

[73] Assignee: Molecular Rx, Inc., Nashville, Tenn.

[21] Appl. No.: 367,235

[22] Filed: Jun. 16, 1989

Related U.S. Application Data

[62] Division of Ser. No. 86,924, Aug. 18, 1987, Pat. No. 4,877,610.

[51] Int. Cl.$^5$ .................. A61K 39/00; A61K 39/085; A61K 39/40; A61K 45/05
[52] U.S. Cl. .................................. 424/88; 424/89; 424/90; 424/92; 424/520; 514/8
[58] Field of Search .................. 424/88–92, 424/95–108

[56] References Cited

U.S. PATENT DOCUMENTS

| | | | |
|---|---|---|---|
| 3,655,874 | 4/1972 | van Hell | 424/99 |
| 4,002,738 | 1/1977 | Johnson et al. | 514/15 |
| 4,005,194 | 1/1977 | Johnson | 514/15 |
| 4,062,942 | 12/1977 | Donini | 424/100 |
| 4,071,622 | 1/1978 | Johnson et al. | 514/15 |
| 4,076,071 | 2/1978 | Burton et al. | 260/112 |
| 4,196,123 | 4/1980 | Rosemberg | 514/12 |
| 4,260,736 | 4/1981 | Asano et al. | 536/5 |
| 4,321,260 | 3/1982 | Auclair | 514/15 |
| 4,384,995 | 5/1983 | Stevens | 424/88 |
| 4,689,222 | 8/1987 | McMichael | 424/88 |
| 4,692,332 | 9/1987 | McMichael | 424/88 |
| 4,877,610 | 10/1989 | McMichael | 424/88 |
| 4,880,626 | 11/1989 | McMichael | 424/88 |

OTHER PUBLICATIONS

Acevedo, et al., *Infection and Immunity*, 31: 487–494 (1981).
Akiyama, et al., *J. Immunol.*, 131: 3085–3090 (1983).
Bogdanov, et al., *FEBS Letters*, 57: 259–261 (1975).
Bogdanov, et al., *Byulleten Eksperimental'noi Biologii i Meditsiny* 84: 709–712 (1977).
Cohen, *British J. Hospital Medicine*, 31: 250–259 (Apr. 1984).
Franklin, *Science News*, 126: 261 (1984).
Gershon, et al., *J. Exp. Med.*, 153: 1533–1546 (1981).
Green, pp. 279–290 in *The Potential Role of T-Cells in Cancer Therapy*, Fefer, et al., eds., Raven Press, New York (1982).
Green, et al., *Ann. Rev. Immunol.*, 1: 439–463 (1983).
Herberman, et al., Chapter 19 in *Immunology III* (Bellanti, ed.), W. B. Saunders Co. (1985), at p. 343.
Herscowitz, Chapter 7 in *Immunology III*, Bellanti, J. W. Saunders, Philadelphia (1985).
Kellen, et al., *Cancer*, 49: 2300–2304 (1982).
Kellen, et al., *Cancer Immunol. Immunother.*, 13: 2–4 (1982).
Kellen, et al., *AACR Abstracts*, 23: 235 (Mar. 1982) (Abstract 928).
Klavins, *Annals of Clinical & Laboratory Science*, 13: 275–280 (1983).
Kölsch, *Scand. J. Immunol.*, 19: 387–393 (1984).
Lewin, Chapter 13 in *Genes*, John Wiley and Sons, New York (1983).
Loblay, et al., *Aust. J. Exp. Biol. Med. Sci.*, 62: 11–25 (1984).
Manzari, et al., *Surv. Immunol. Res.*, 1: 122–125 (1982).
Miller, *Clinical Medicine*, 81: 16–19 (1974).
Morgan, et al., *J. Virol.*, 46: 177–186 (1983).
Simon, et al., *JMCI*, 70: 839–845 (1983).
Yamauchi, et al., *J. Exp. Med.*, 153: 1547–1561 (1981).
Abstract of examined Japanese Pat. Appln. No. 84 046487 (published Nov. 13, 1984).
Green, et al., *Proc. Nat. Acad. Sci.* (U.S.A.), 73: 381–385 (1976).
"Bacterial Antigen Made from Staphylococcus" (Leaflet P–108A), published Nov. 1982 by Delmont Laboratories, Inc., Swarthmore, Pennsylvania 19081.

*Primary Examiner*—Ronald W. Griffin
*Attorney, Agent, or Firm*—Marshall, O'Toole, Gerstein, Murray & Bicknell

[57] ABSTRACT

A method and composition for treating malignant neoplasia and acquired immune deficiency syndrome by once daily administration of a substance (such as human chorionic gonadotropin) characteristic of the tumor or acquired immune deficiency syndrome-afflicted cell in an amount less than the lowest amount necessary to provoke a humoral immune response, as exemplified by the existence of a negative wheal upon subcutaneous administration.

36 Claims, No Drawings

IMMUNOTHERAPEUTIC METHODS AND COMPOSITIONS EMPLOYING ANTIGENS CHARACTERISTIC OF MALIGNANT NEOPLASMS

This is a division of application Ser. No. 086,924, filed Aug. 18, 1987, now U.S. Pat. No. 4,877,610.

BACKGROUND OF THE INVENTION

The present invention pertains in general to immunotherapeutic techniques for alleviating the symptoms of malignant neoplasia and for treating diseases of viral origin. In particular, the present invention pertains to immunotherapeutic techniques useful in treatment of disease states such as feline leukemia, bovine leukemia and the acquired immune deficiency syndrome (AIDS).

In order to protect the integrity of the organism, higher vertebrates possess an elaborate immune system which distinguishes foreign substances, which must provoke an immune response in order to be eliminated, from "self" substances, which are tolerated. The mechanism that effectuates this discrimination between self and foreign substances is known to involve interactions among types of white blood cells (leukocytes).

Upon exposure of the antigen to the circulating fluids of the body, substances capable of recognition by the immune system (antigens) come into contact with a type of leukocytes called a macrophage. Macrophages are phagocytic cells and can therefore engulf and destroy materials which are not protected from them by size, surface texture (i.e., smoothness), surface charge, or some other mechanism.

Once engulfed and processed by a macrophage, an antigen or a portion thereof is presented at the surface of the macrophage for contact with another type of leukocyte called a thymocyte or T-cell. T-cells control the production of antibodies by yet another type of lymphocyte called a B-cell.

Antibodies are B-cell-produced proteins which are capable of combining with an antigen in a reaction which is specific for that antigen. An antibody only combines with certain portions (antigenic determinants) of the surface of the antigen, so that the antibody is specific to the degree that the determinant with which it combines is not also found on other antigens.

The binding of an antibody to its corresponding antigen on the surface of a foreign cell has significant consequences related to the destruction of that cell by the immune system. First, the coating of the cell by antibody facilitates ingestion of the cell by macrophages and by other types of phagocytes including killer (K) cells, which act to destroy antibody-coated cells but which do not require sensitization by prior exposure with macrophage-processed antigen, and polymorphonuclear (PMN) leukocytes. Second, the coating of a cell by antibody activates a system of proteins, known as the complement system, in the liquid (plasma) fraction of the blood. Upon activation of this system, complement components also coat the foreign cell, which facilitates phagocytosis. In addition, complement activation results in the stimulation of inflammatory cells, leading to production of chemicals which attract macrophages through a process called chemotaxis and leading to inflammatory hormone-like activation of cellular functions. Lastly, complement components act directly to break up (lyse) the membrane of the foreign cell. The portion of the immune response involved with antigen-antibody and complement interactions is generally referred to as the humoral reaction.

T-cells, which regulate the humoral reaction, are of several types. These types of T-cells have been described as including helper ($T_H$) cells, inducer ($T_I$) cells, regulator ($T_R$) cells, and suppressor ($T_S$) cells. [Herscowitz, Chapter 7 in *Immunology III*, Bellanti, J. W. Saunders, Philadelphia (1985)]. $T_I$ and $T_H$ cells are mobilized by contact with processed antigen on the surface of macrophages. $T_H$ cells are also activated by signals from $T_I$ and from $T_R$ cells. $T_R$ cells are activated by signals from $T_I$ and $T_S$ cells. Mobilization of $T_S$ cells occurs in response to signals from $T_R$ cells or as a result of contact with antigen.

Introduction of an optimal amount of a foreign substance into the fluids of the body initiates a process which results in production of antibody by B-cells. In this process, B-cells respond to stimulation by $T_H$ cells, which have in turn been stimulated by macrophages. Introduction of a persistent low level of some antigens or of a high level of an antigen results in a low-level of or in a lack of production of antibody due to an interruption by $T_S$ cells of the signals from $T_H$ cells to B-cells. This interruption, called suppression, may be induced through the macrophage-$T_I$-$T_R$ pathway or by direct stimulation of the $T_S$ cells by antigen. Suppression of antibody production to a first antigen may be overcome in a process known as contrasuppression through the stimulation of a subtype of $T_S$ cells called contrasuppressor cells by a second antigen which is antigenically similar to the first antigen. These contrasuppressor cells send a signal to $T_R$ cells which render the $T_H$ cells resistant to the activity of the suppressor $T_S$ cells and which interrupt the suppressor signals of the suppressor $T_S$ cells. See Gershon, et al., *J. Exp. Med.*, 153: 1533–1546 (1981); Yamauchi, et al., *J. Exp. Med.*, 153: 1547–1561 (1981); and Green, et al., *Ann. Rev. Immunol.*, 1: 439–463 (1983).

It is the balance of the actions of $T_H$ helper and $T_S$ suppressor cells which determines whether or not an immune response develops in the presence of an antigen. Thus, as a practical matter, the functioning of the network of T-cells may be viewed in terms of the ratio of helper to suppressor cells ($T_H/T_S$).

T-cells are also involved in another type of immune response, which is said to involve cell-mediated immune (CMI) reactions. Contact of $T_H$ cells with macrophage-processed antigen causes the $T_H$ cells to release interleukin II (IL-2), which activates cytotoxic ($T_{CYT}$) T-cells and, in conjunction with gamma interferon also released by the $T_H$ cells at this time, activates natural killer (NK) cells. Both $T_{CYT}$ and NK cells kill foreign cells. $T_{CYT}$ cells are particularly involved with rejection and the destruction of tumor cells.

As is evident from the foregoing discussion, a general outline of the functioning of the immune system is available. However, many areas of the functioning of the immune system remain unclear. One of these areas relates to the inability of the immune system to recognize certain cancers (malignant neoplasms) and cells infected with certain viruses [e.g., feline leukemia virus; bovine leukemia virus; and human T-leukemia-lymphoma virus (HTLV), which is believed to be the causative agent in AIDS].

In attempts to stimulate an immune response against a malignant neoplasm, many approaches have been aimed at the augmentation of antitumor defenses by administration of adjuvants (immune enhancers or potentiators). These approaches attempt to enhance nonspecific phagocytosis and killing of tumor cells by macrophages and T-cells. Such approaches employ infectious BCG mycobacteria, non-living *Corynebacterium parvum*, glucan (a glucose polymer derived from microorganisms), or levamisole (an antihelminthic drug known to be useful for stimulating CMI and the action of macrophages). Herberman, et al., Chapter 19 in *Immunology III* (Bellanti, ed.), W. B. Saunders Co. (1985), at page 343. The reported antitumor action of lysosome and pepsin lysates containing glycopeptides from the cell wall of *Lactobacillus bulgaricus* [Bogdanov, et al., *FEBS Letters*, 57: 259 (1975); Bogdanov, et al., *Byulletin Eksperimental'noi Biologia i Meditsiiny*, 84: 709 (1977)] and the treatment of malignant tumors with destroyed *Staphylococcus aureus* [abstract of examined Japanese Patent Application No. 84 046487] appear to fall in this category. Adjuvant therapy has had varying degrees of questionable or limited success. Herberman, et al., supra.

The failure of the immune system to recognize malignant neoplasms is particularly puzzling in view of the fact that certain characteristic substances (tumor markers) are present at levels which are elevated above normal in patients with various neoplastic disease states. Specifically, alphafetoprotein (AFP), Carcinoembryonic antigen (CEA), and human chorionic gonadotropin (HCG) are oncofetal tumor markers widely used in the investigation of patients with neoplasms of the liver, colon, and trophoblast, respectively. AFP has been found at levels elevated above normal in fifty percent or more of patients with yolk sac tumors, hepatomas, retinoblastomas, embryonal carcinomas, breast carcinomas, and carcinomas of the uterine cervix, and has been found at elevated levels in between two and fifty percent of patients having carcinomas of the pancreas, melanomas, gastric carcinomas, basal cell carcinomas, bronchogenic carcinomas, leukemias, colon carcinomas, and nasopharyngeal carcinomas. CEA has been found at elevated levels in fifty percent or more of patients having colon carcinomas, choriocarcinomas, pancreatic carcinomas, medullary thyroid carcinomas, familial medullary thyroid carcinomas, osteosarcomas, retinoblastoms, ovarian cystadenocarcinomas, mycosis fungoides, hepatomas, esophageal carcinomas, adenocarcinomas of the uterine cervix, lung carcinomas, carcinomas of the small intestine, urinary bladder carcinomas, and renal cell carcinomas, and has been found at elevated levels in between nine and fifty percent of patients having neural crest tumors, breast carcinomas, prostatic carcinomas, primary uveal carcinomas, neuroblastomas, fluids with malignancy, seminomas, basal cell carcinomas, gastric carcinomas, laryngeal carcinomas, endometrial carcinomas, uterine cervix intraepithelial carcinomas, carcinomas of the buccal mucosa, craniopharyngiomas, embryonal rhabdomyosarcomas, carcinomas of the oropharynx, brain tumors and testicular teratomas. HCG has been found at elevated levels in the serum of fifty percent or more of patients having choriocarcinomas, malignant interstitial cell tumors of the testis, non seminomatous tumors of the testis, embryonal carcinomas, and pancreatic carcinomas, and has been found at elevated levels in between six and fifty percent of the patients having teratomas, ovarian adenocarcinomas, uterine cervix carcinomas, endometrial carcinomas, seminomas, gastric carcinomas, urinary bladder carcinomas, breast carcinomas, colorectal carcinomas, bronchogenic squamous cell carcinomas, mellanomas, and multiple myelomas. Other universal oncofetal tumor markers, including tissue polypeptide antigen (TPA), which is associated with cell proliferation and which is not specific for any species, are also known. See, Klavins, *Annals of Clinical and Laboratory Science*, 13: 275–280 (1983).

With respect to HGC, a chorionic gonadotropin-like antigen has been found in bacteria isolated from the urine of cancer patients, as indicated in Acevedo, et al., *Infection and Immunity*, 31: 487–494 (1981), but not in the same species of bacteria obtained from any other source tested. Furthermore, rat mammary adenocarcinoma cells and rat hepatoma cells have been found to synthesize chorionic gonadotropin-like material, although no such material was found in the sera of the animals bearing these neoplasms, in Kellen, et al., *Cancer*, 49: 2300–2304 (1982); and in Kellen, et al., *Cancer Immunol. Immunother.*, 13: 2–4 (1982). In the papers of Kellen, et al., and in U.S. Pat. No. 4,384,995, a subunit of HCG conjugated to tetanus toxoid is used to prophylactically stimulate an immune response to chorionic gonadotropin-like substances by repeated injection with the conjugated material before exposure to tumor cells known to bear a chorionic gonadotropin-like antigen.

Among the differences between prophylactic treatment with HCG and the adjuvant therapy approach is that the induction of an immune response for prophylactic purposes requires repeated injections over a period of time in order to initiate the development of at least one population of identical B-cells (a clone) producing a given antibody to a tumor antigen and for antibody to be produced by that clone. On the other hand, adjuvant therapy may result in antibody production by an existing clone of B-cells and thus has antitumor effects which may be immediately observed. Therapeutic treatment (i.e., treatment after a malignant neoplasm is present) with HCG conjugated with tetanus toxoid raises the possibility of an uncontrollable Herxheimer-type reaction. The Herxheimer reaction appears after treatment of syphilis patients with a substance that is toxic to the causative spirochete bacteria, which thereupon die in massive numbers, releasing potentially fatal toxic substances into the blood stream. By analogy, at some as-yet unpredictable point in the induction of an immune response to a tumor antigen, a massive die-off of cancer cells may result in the death of the patient.

A luteinizing hormone releasing factor (LHRF), sometimes generically referred to as gonadorelin, which causes luteinizing hormone, a pituitary gonadotropin, to be released from the pituitary, has been used for treating various tumors in U.S. Pat. Nos. 4,002,738 and 4,071,622. Gonadorelin has also been used in the treatment of benign prostatic hyperplasia, a type of non-malignant but excess prostatic growth, in U.S. Pat. No. 4,321,260. However, no indication is provided in these patents that direct application of any gonadotropin may affect destruction of malignant neoplasms. In addition, release of LH from the pituitary is subject to a feedback control independent of the administered gonadotropin, so that how much, if any, LH is released is not determinable merely from knowledge of an administered dose. Moreover, LHRF in combination with other substances may act to increase chorionic gonadotropin secretion by direct action on a tumor cell, further compounding the uncertain effect of LHRF administration. Kellen, et al., *AACR Abstracts*, 23: 235 (Mar. 1982) (Abstract 928).

In fact, Simon, et al., *J.M.C.I.*, 70: 839–845 (1983), indicate that dosages of gonadotropic and steroid hormones stimulate the growth of differentiated carcinomas. These hormones included human follicle-stimulating hormone (FSH), HCG, human luteinizing hormone (LH), and cortisol. Thus Simon, et al. appears to support the idea that direct administration of gonadotropic or steroid hormones has a proliferative effect on malignant neoplasms.

Evidence for the suppression of the immune response against antigens of neoplastic cells is provided by Akiyama, et al., *J. Immunol.*, 131: 3085–3090 (1983), wherein responsiveness of a mixed culture of lymphocytes from cancer patients and healthy donors was suppressed by the introduction into the system of tumor cells from the cancer patients. This suggests that among the lymphocytes of the cancer patients were $T_S$ cells specific for tumor-derived cells, inasmuch as the response of cultures containing only lymphocytes from healthy donors was not so suppressed.

Furthermore, antigen-specific $T_S$ cells have been isolated from a mouse having a plasmacytoma, which cells inhibited the in vitro induction of a cytotoxic T-cell response against the tumor. Kölsch, *Scand. J. Immunol.*, 19: 387–393 (1984). According to Kölsch, $T_S$ cells may be activated and may dominate $T_H$ cells by high and low doses of antigen, but a critical, intermediate antigen dose which activates $T_H$ cells at the same time as it activates the $T_S$ cells, permits $T_H$ cells to dominate. Thus, Kölsch indicates that there may be an antigen dose at which a delicate balance is reached where $T_H$ cells are activated but at which $T_S$ cells dominate the immune response.

In Loblay, et al., *Aust. J. Exp. Biol. Med. Sci.*, 62: 11–25 (1984), it is indicated that the suppression produced by $T_S$ cells in animals which have been exposed to an antigen is enhanced by a subsequent administration of a sufficiently large dose of antigen. Perhaps it is not so surprising, therefore, that attempts to induce contrasuppression have been aimed at supplying contrasuppressor cells, or substances therefrom, rather than by direct induction of contrasuppression. See, Green, "Contrasuppression: Its Role in Immunoregulation", in *The Potential Role of T-Cells in Cancer Therapy*, Fefer, et al., eds., Raven Press, New York (1982); and Green, et al., *Ann. Rev. Immunol.*, 1: 439–463 (1983).

SUMMARY OF THE INVENTION

Accordingly, a method according to the present invention for alleviating symptoms of malignant neoplasia in a disease victim comprises the step of administering to the disease victim a member selected from the group consisting of characteristic substances of diseased cells of the malignant neoplasia victim and effective fragments and effective derivatives thereof, in an amount which is less than the lowest amount necessary to provoke a humoral immune response, as exemplified by the determination of a positive wheal upon subcutaneous injection. Illustrative of such a method is the once daily administration of a composition including HCG and a lysate of *S. aureus*.

A further method according to the present invention for alleviating symptoms of acquired immune deficiency syndrome in a disease victim comprises the step of administering to the disease victim a member selected from the group consisting of characteristic substances of diseased cells of the acquired immune deficiency syndrome victim and effective fragments and effective derivatives thereof, in an amount which is less than the lowest amount necessary to provoke a humoral immune reponse, as exemplified by the determination of a positive wheal upon subcutaneous injection.

A composition according to the present invention for alleviating symptoms of malignant neoplasia in a disease victim comprises a member selected from the group consisting of characteristic substances of diseased cells of the malignant neoplasia victim and effective fragments and effective derivatives thereof, in an amount which is less than the lowest amount of the substance necessary to induce a humoral immune response. The composition according to the present invention also comprises an immune enhancer in an amount less than the lowest amount of the substance necessary to provoke a humoral immune response, as exemplified by the determination of a positive wheal upon subcutaneous injection. Illustrative of such a composition are compositions including HCG and a lysate of *S. aureus*.

A further composition according to the present invention for alleviating symptoms of acquired immune deficiency syndrome in a disease victim comprises a member selected from the group consisting of characteristic substances of diseased cells of the acquired immune deficiency syndrome victim and effective fragments and effective derivatives thereof, in an amount which is less than the lowest amount of the substance necessary to induce a humoral immune response. This composition also comprises an immune enhancer in an amount less than the lowest amount of the substance necessary to provoke a humoral immune response, as exemplified by the determination of a positive wheal upon subcutaneous injection. Illustrative of such a composition are compositions including HCG and a lysate of *S. aureus*.

DESCRIPTION OF THE PREFERRED EMBODIMENT

In a method according to the present invention, a substance characteristic of malignant neoplasia or AIDS is respectively administered to a victim of malignant neoplasia or AIDS in an amount which is believed to be less than the lowest amount necessary to provoke a humoral immune response (that is, to begin production of antibody). This dosage is administered daily until disappearance of the symptoms of the disease, and may be administered longer without harm if so desired.

In order to identify a dose lower than that required to provoke a humoral immune response, a wheal produced upon subcutaneous injection of the therapeutic material is evaluated according to the procedure set forth in Moore, *Clinical Medicine*, 81, 16–19 (1974), wherein such evaluation is employed to identify a dosage of vaccine useful in the eradication of the symptoms of influenza. Upon subcutaneous injection, a wheal may be determined to be positive ten minutes after injection as blanched, hard, raised and discoid (regular, sharply demarcated edges, as though a disc has been cemented to the skin). A negative wheal, indicative of a dose below that necessary to provoke an immune response, is so absorbed at the end of ten minutes that it is softer and flatter than at injection, may have an irregular or ragged edge, and has grown less than an average of two millimeters in diameter.

Although the preferred dosage of 2 International Units (IU) was initially determined by skin tests of the horse of Example 1, the Examples below indicate that successful therapy may often be achieved by administering a dose at a level of 2 IU. A dose of 2 IU appeared to be low enough for any animal or human tested, even without first determining optimum dose by a skin test. However, it is believed that determination of a proper dosage, as exemplified above or otherwise, may be used by those skilled in the art to refine the method according to the present invention.

To complement the activity of the chorionic gonadotropin, and to simultaneously guard against a toxic reaction induced by a rapid sloughing of necrotic tissue analogous to a Herxheimer-type reaction, a bacterial lysate was added to each treatment vial as a broad-spectrum stimulator of cell-mediated immunity. No species specificity of response was observed, to the extent that a human has responded to either of equine chorionic gonadotropin (ECG) or HCG, and that other animals of the examples have also responded favorably to treatment with either ECG or HCG.

AIDS patients have been reported as exhibiting a marked reduction in the ratio of $T_H$ to $T_S$ cells. See, Cohen, *British Journal of Hospital Medicine*, 31, 250–259 (1984). AIDS has been defined as a disease at least moderately predictive of a defect in cell-mediated immunity, occurring in a person with no known cause for diminished resistance to that disease by the Centers for Disease Control.

It has been reported that the virus thought to cause AIDS is a type of human T-cell leukemia-lymphoma virus (HTLV) known as HTLV-III virus and that this virus is related to the virus which causes feline and bovine leukemia. Franklin, *Science News*, 126, 261 (1984). Feline and bovine leukemia viruses are known to be antigenically similar. Morgan, et al., *J. Virol.*, 46: 177–186 (1983). Accordingly, the discovery by the present inventor that a dose of HCG which is lower than that required to provoke a humoral immune response may be effective in the alleviation of the symptoms of feline leukemia and of bovine leukemia, indicates the potential effectiveness of an analogous form of treatment in the alleviation of the symptoms of AIDS as well.

Furthermore, feline leukemia virus (FLV) and HTLV are both retroviruses (also known as Type C viruses, RNA tumor viruses, leukemia viruses). Manzani, et al., *Surv. Immunol. Res.*, 1: 122–125 (1982). A retrovirus may be transmitted as an infectious particle containing viral genes encoded in the form of ribonucleic acid (RNA). Within an infected cell this RNA is encoded into deoxyribonucleic acid (DNA) by a viral enzyme called reverse transcriptase. The DNA-encoded viral genes are thereafter integrated with and replicated, transcribed and translated along with the DNA-encoded genetic material of the infected cell. Lewin, Chapter 13 in *Genes*, John Wiley and Sons, New York (1983). Such retroviruses generally produce steady state infections where viral progeny are continually extruded by budding from the surfaces of host cells. In this way, steady state viruses exhibit the clinical criteria for the induction of tolerance in that there is a high dose inoculum of viral antigen, the virus-specific antigen persists, and tumor-specific antigens are developed and persist. See Herberman, et al., supra.

Therefore, the methods and compositions according to the present invention which are shown in the examples below to be effective in the treatment of feline and bovine leukemia, among other neoplastic diseases, are also expected to be effective in the treatment of AIDS.

Examples 1, 2 and 3 below relate to the treatment of horses afflicted with two different types of malignant neoplasms.

Examples 4 and 5 below relate to the treatment of cats diagnosed as having feline leukemia.

Example 6 below relates to the treatment of cows afflicted with bovine leukemia.

Examples 7 and 8 below relate to the treatment of dogs afflicted with two different types of malignant neoplasm.

Example 9 below relates to the treatment of human patients afflicted with malignant neoplasms.

EXAMPLE 1

A horse with mastocytoma was treated with 2 IU per day of gonadotropin only (i.e., without the bacterial lysate immune enhancer). The gonadotropin used was equine chorionic gonadotropin, supplied by the W. A. Butler Company, or human chorionic gonadotropin, supplied by the Ayerst Corp. (as A.P.L.—human chorionic gonadotropin). In this example and in the examples which follow, a dosage of 2 IU per day of either equine chorionic gonadotropin (ECG) or HCG was used.

The horse showed rapid and significant diminution of tumors before succumbing to an Herxheimer-type reaction. (No such adverse effect was seen in other treated animals where an immune enhancer was used.)

EXAMPLE 2

Three horses with melanoma were successfully treated to the point of the disappearance of symptoms according to the procedure of Example 1 above, but with the addition of a bacterial lysate immune enhancer.

After the symptoms disappeared, the three animals received no further treatment but exhibited no recurrence of symptoms.

A suitable bacterial lysate for employment in this procedure is sold under the name Staphage Lysate ™, available from Delmont Labs. Staphage Lysate ™ is a bacteriologically sterile staphylococcal vaccine containing components of *Staphylococcus aureus* and culture medium ingredients (sodium chloride and ultrafiltered beef heart infusion broth). The staphylococcal components are prepared by lysing parent cultures of *S. aureus*, serologic types II and III, with a polyvalent staphylococcus bacteriophage. Each milliliter contains 120–180 million colony-forming units of *S. aureus* and 100–1000 million staphylococcus bacteriophage plaque-forming units.

All treatment trials contained two units of gonadotropin plus 0.1 cc Staphage Lysate ™ in each 0.5 cc shot.

ADMINISTRATION OF MATERIALS

Regardless of species, type of malignancy, or size of cancer, all animals received a once-daily subcutaneous injection of the admixture of chorionic gonadotropin and immune enhancer until the tumor or leukemia had disappeared.

TESTS AND RESULTS

All animals were diagnosed as having cancer by a licensed veterinarian.

EXAMPLE 3

One horse with an undifferentiated carcinoma of the face was successfully treated according to the procedure of Example 2 to the point of the disappearance of symptoms. After disappearance of the symptoms, the horse received no further treatment but exhibited no recurrence of symptoms.

EXAMPLE 4

A double-blind test of treatment of cats diagnosed as being infected with feline leukemia virus was conducted by a licensed testing laboratory. Laboratory tests for feline leukemia were conducted by a licensed laboratory, and biopsy tissue from some cases was examined by a veterinary reference laboratory. In all cases animals were treated as above, with termination of treatment coinciding with disappearance of symptoms. In no cases was it necessary to resume therapy for a second round of treatment. No side effects have been observed.

All animals receiving a placebo died within 7 days. Some treated animals were still alive after six weeks, and were receiving no further treatment. Of special interest was the observation that several treated cats were not only asymptomatic, but also non-viremic. In any event, survival was prolonged and/or symptoms were alleviated for 6 (cats numbered 2, 3, 11, 21, 23 and 24) of 8 treated animals, as compared to the animals receiving a placebo.

Cats numbered 4, 5, 16 and 22 received a placebo.

Cat number 4 died one day after the start of the test. Cat number 4 was not necropsied.

Cat number 5 showed no significant change in viremia. Tumor size remained constant. The cat was euthanized on day 10 of the test. At necropsy, the cat was observed to be moribund, thin, blind and anemic. Tumors were located on the tongue, eyes, pleural cavity, peririnal and peritoneal cavity.

Cat number 16 died six days after initial treatment. Upon necropsy, small metastatic tumors were observed in the lungs, and large tumors were observed in the omentum.

Cat number 22 died six days after initial treatment. Upon necropsy, metastatic tumors were found in the lung, in the liver and in the omentum. The cause of death was renal hemorrhage into the retroperitoneal sublumbar region.

Cats numbered 2, 3, 7, 11, 15, 21, 23 and 24 received the experimental treatment.

In cat number 2, viremia decreased but the tumor remained the same size. Cat number 2 died 16 days after the start of the test. At necropsy, a tumor was found which was open and which had drained. General lymph node enlargement, an enlarged liver, and a small tumor in the apex of the heart were also noted.

In cat number 3, viremia decreased to negative. The tumor decreased in size back to a normal condition. The cat was normal in appearance during the test.

Cat number 7 died four days after initial treatment. No necropsy was performed.

Cat number 11 exhibited a slight decrease in viremia. Tumor size remained the same. Cat number 11 died 19 days after initial treatment. Upon necropsy, tumors were found throughout the body cavity.

Cat number 15 showed no significant decrease in viremia. No change in the tumor was observed. The cat died ten days after initial treatment. At necropsy, the cat was observed to be emaciated, and tumors were found in the lungs, mediastinum, pericardia, pleura and illiac lymph nodes.

In cat number 21 the viremia was constant. The cat appeared normal. Upon necropsy, an enlarged thymus and enlarged mesenteric lymph nodes were observed.

In cat number 23, viremia decreased through the course of the test. Cat number 23 remained normal throughout the duration of the test.

In cat number 24, viremia remained constant. The cat appeared normal throughout the duration of the test. Upon necropsy, an enlarged thymus was observed, but the cat was otherwise normal.

EXAMPLE 5

Several dozen cats have been successfully treated according to the procedure of Example 2 above by veterinarians in Ohio, Pennsylvania and North Carolina for feline leukemia. Based upon the reported observations of the veterinarians, at least 80% and have returned to normal health after terminating therapy. For example, one cat had strength only to lift its chest wall to breathe, and its body weight was reduced from 13 pounds to 6 pounds. After ten days of therapy, the cat was mobile and active, and its weight had increased to ten pounds.

EXAMPLE 6

Twenty cases of bovine leukemia were treated according to the procedure of Example 2 above, with complete remission of symptoms for as long as 13 months. Milk production of 17 cows was both restored and enhanced. Only three failures occurred, and in each case the cow had been moribund for several days before initiation of therapy. Laboratory tests for bovine leukemia were conducted by a licensed laboratory, and biopsy tissue from some cases was examined by a veterinary reference laboratory.

EXAMPLE 7

A squamous cell carcinoma on the jaw of a six-month-old pup was treated according to the procedure of Example 2 above. In spite of a "poor prognosis" from the veterinary reference laboratory examining the biopsy tissue, the dog entirely healed, as evidenced by sequential X-ray records. The dog has since been without treatment for nearly one year.

A squamous cell carcinoma on the shoulder of a 12-year-old dog was treated according to the procedure of Example 2 above. After two days the dog could walk for extended periods, ate well, and the tumor became warm to the touch. Noticeable tumor shrinkage was observed after five days. After two weeks, the tumor was nearly resolved.

EXAMPLE 8

An anal tumor growing daily and laterally displacing the tail of a 13-year-old dog was treated according to the procedure of Example 2 above. The photographic record showed daily decrease in tumor size beginning on day three. The tumor resolved. The dog later died for unknown reasons. No necropsy was performed.

EXAMPLE 9

A limited number of human patients have been treated for cancers diagnosed as terminal, including melanoma and cancers of the colon, breast, liver, pancreas and lung. The patients were treated according to the procedure of Example 2 above, except that some patients received 0.2 cc of immune enhancer per dose.

Of 9 patients treated at one location within a period of $2\frac{1}{2}$ years, all lived longer than the expected survival time indicated by their treating physicians, and only one died. The patient who died had discontinued treatment according to the present invention two months before death. Of the 8 surviving patients, 6 have survived 1½ years or more since beginning treatment.

All 9 patients practiced the method according to the present invention as a last resort, and all but the one patient who died had had some form of radiation or chemotherapy prior to beginning therapy according to the present invention. All 9 patients had diagnosed metastases indicative of an advanced disease state. No side effects were observed.

It is not clear, however, how regularly all patients administered the composition according to the present invention. For example, some surviving patients have decreased treatment to once or twice per week without reduction in overall well-being. None of these patients (except for the one patient who died) is known to have entirely discontinued treatment.

Sporadic treatment at other locations has not been as successful, so that overall, about half of the treated patients are still surviving, while the other half have died. Due to the lack of autopsy data, it is not clear whether or not all of the deaths of treated patients may properly be attributed to cancer or to other causes.

Patients who had not received maximum chemotherapy and radiation responded most positively to the composition and method of the present invention. This suggests that the therapeutic agent of the present invention involves, at least in part, immune manipulation, and that the cells comprising the immune response in patients receiving traditional anti-cancer therapy are compromised.

The effectiveness of treatment of malignant neoplasms, feline leukemia, and AIDS with gonadotropins may be explained in a number of ways. The rapidity of the response achieved according to the present invention, even with administration of HCG alone as in Example 3, suggests that the present invention is not operating merely by the initiation of a humoral immune response. One explanation is that the low dosage of gonadotropin stimulates a contrasuppression reaction by tipping the balance of the $T_H/T_S$ ratio in favor of activation of $T_H$ cells, and that this leads to the release of a pre-existing immune response (including a CMI response) against the disease. Another explanation may be that the gonadotropin acts in a negative feedback mechanism to turn off production of gonadotropin-like molecules by the malignant cells, leading to a reduction in gonadotropin-like cells on the surface of the malignant cells, leading in turn to a change in the surface charge from the negative charge associated with gonadotropin-like molecules to a more positive charge which facilitates ingestion by macrophages, or leading to exposure of otherwise hidden tumor antigens. However, it is not intended that the present invention be limited to any explanation.

While the present invention has been described in terms of specific methods and compositions, it is understood that variations and modifications will occur to those skilled in the art upon consideration of the present invention.

For example, it is envisioned that various derivatives and fragments of the recited human chorionic gonadotropin and other tumor- or viral-specific antigens will be effective according to the present invention. In addition, although the preferred route of administration is by subcutaneous injection, it is not intended to preclude intramuscular, intraperitoneal, or intravenous injection, intranasal administration, or any other effective route of administration from being included within the scope of the present invention.

Also, inasmuch as other tumor markers, such as carcinoembryonic antigen, alphafetoprotein and tissue polypeptide antigen, are classified with HCG in relation to appearance in association with malignant neoplasms and are, therefore, likely to be similarly effective, it is intended that these substances be included within the scope of the present invention as well.

Furthermore, human chorionic gonadotropin, follicle-stimulating hormone, luteinizing hormone and thyroid-stimulating hormone are each glycoproteins composed of an $\alpha$ and a $\beta$ subunit. The $\alpha$ subunit of HCG differs only slightly from an $\alpha$ subunit which is identical in each of FSH, LH and TSH. Although the significance of the subunit structure is yet to be determined, both $\alpha$- and $\beta$-HCG have been associated with tumors. See Acevedo, et al., *Infection and Immunity*, 31: 487-494 (1981). Accordingly, it is intended that these pituitary hormones be included within the scope of the present invention.

It is contemplated that effective fragments and effective derivatives of all of the foregoing suggested substances will be manufactured by those skilled in the art and employed according to the present invention. These fragments and derivatives are also intended to come within the scope of the invention as claimed.

Accordingly, it is intended in the appended claims to cover all such equivalent variations which come within the scope of the invention as claimed.

What is claimed is:

1. A method for alleviating/alleviating symptoms of malignant neoplasia in a human disease victim comprising the step of administering to said disease victim a member selected from the group consisting of characteristic substances of diseased cells of malignant neoplasia and effective fragments and effective derivatives thereof, in an amount which is less than the lowest amount necessary to provoke a humoral immune response, as exemplified by the presence of a positive wheal upon subcutaneous administration.

2. The method as recited in claim 1 wherein said characteristic substance is a glycoprotein.

3. The method as recited in claim 2 wherein said glycoprotein is a gonadotropin.

4. The method as recited in claim 3 wherein said glycoprotein is a chorionic gonadotropin.

5. The method as recited in claim 4 wherein said gonadotropin is a member selected from the group consisting of human chorionic gonadotropin and equine chorionic gonadotropin.

6. The method as recited in claim 5 wherein said immune enhancer is a bacterial lysate.

7. The method according to claim 6 wherein said bacterial lysate is a lysate of *Staphylococcus aureus*.

8. The method as recited in claim 3 wherein said gonadotropin is a pituitary gonadotropin.

9. The method as recited in claim 8 wherein said pituitary gonadotropin is a member selected from the group consisting of luteinizing hormone and follicle stimulating hormone.

10. The method according to claim 9 further comprising the step of co-administering an immune enhancer in an amount which is less than the lowest amount necessary to provoke a humoral immune response in combination with the characteristic substance, as exemplified by the presence of a positive wheal upon subcutaneous administration.

11. The method according to claim 10 wherein said immune enhancer is a bacterial lysate.

12. The method according to claim 11 wherein said bacterial lysate is a lysate of *Staphylococcus aureus*.

13. The method as recited in claim 2 wherein said glycoprotein is thyroid-stimulating hormone.

14. The method according to claim 13 further comprising the step of co-administering an immune enhancer in an amount which is less than the lowest amount necessary to provoke a humoral immune response in combination with the characteristic substance, as exemplified by the presence of a positive wheal upon subcutaneous administration.

15. The method according to claim 14 wherein said immune enhancer is a bacterial lysate.

16. The method according to claim 15 wherein said bacterial lysate is a lysate of *Staphylococcus aureus*.

17. The method as recited in claim 1 wherein said characteristic substance is a member selected from the group consisting of carcinoembryonic antigen, alphafetoprotein, and tissue polypeptide antigen.

18. The method according to claim 17 further comprising the step of co-administering an immune enhancer in an amount which is less than the lowest amount necessary to provoke a humoral immune response in combination with the characteristic substance, as exemplified by the presence of a positive wheal upon subcutaneous administration.

19. The method according to claim 18 wherein said immune enhancer is a bacterial lysate.

20. The method according to claim 19 wherein said bacterial lysate is a lysate of *Staphylococcus aureus*.

21. A pharmaceutical preparation for alleviating non-pain symptoms of malignant neoplasia in a human disease victim comprising:
   a member selected from the group consisting of characteristic substances of diseased cells of malignant neoplasia and effective fragments and effective derivatives thereof, in an amount which is less than the lowest amount of the substance necessary to provoke a humoral immune response, as exemplified by the presence of a positive wheal upon subcutaneous administration; and
   an immune enhancer in an amount less than the lowest amount of the substance necessary to induce a humoral immune response in combination with said characteristic substance, as exemplified by the presence of a positive wheal upon subcutaneous administration.

22. The pharmaceutical preparation as recited in claim 21 wherein said characteristic substance is a glycoprotein.

23. The pharmaceutical preparation as recited in claim 22 wherein said glycoprotein is a gonadotropin.

24. The pharmaceutical preparation as recited in claim 23 wherein said glycoprotein is a chorionic gonadotropin.

25. The pharmaceutical preparation as recited in claim 24 wherein said immune enhancer is a bacterial lysate.

26. The pharmaceutical preparation according to claim 25 wherein said bacterial lysate is a lysate of *Staphylococcus aureus*.

27. The pharmaceutical preparation as recited in claim 23 wherein said gonadotropin is a pituitary gonadotropin.

28. The pharmaceutical preparation as recited in claim 27 wherein said pituitary gonadotropin is a member selected from the group consisting of luteinizing hormone and follicle stimulating hormone.

29. The pharmaceutical preparation according to claim 28 wherein said immune enhancer is a bacterial lysate.

30. The pharmaceutical preparation according to claim 29 wherein said bacterial lysate is a lysate of *Staphylococcus aureus*.

31. The pharmaceutical preparation as recited in claim 22 wherein said glycoprotein is thyroid-stimulating hormone.

32. The pharmaceutical preparation according to claim 31 wherein said immune enhancer is a bacterial lysate.

33. The pharmaceutical preparation according to claim 32 wherein said bacterial lysate is a lysate of *Staphylococcus aureus*.

34. The pharmaceutical preparation as recited in claim 21 wherein said characteristic substance is a member selected from the group consisting of carcinoembryonic antigen, alphafetoprotein, and tissue polypeptide antigen.

35. The pharmaceutical preparation according to claim 34 wherein said immune enhancer is a bacterial lysate.

36. The pharmaceutical preparation according to claim 35 wherein said bacterial lysate is a lysate of *Staphylococcus aureus*.

* * * * *